United States Patent
Ortiz et al.

(10) Patent No.: US 11,946,091 B2
(45) Date of Patent: Apr. 2, 2024

(54) METHODS FOR PROCESSING PLANT MATERIALS AND PRODUCING DRIED PRODUCTS

(71) Applicant: E. & J. Gallo Winery, Modesto, CA (US)

(72) Inventors: Jorge Ortiz, Fresno, CA (US); Nathan Keeley, Fresno, CA (US); Dan Burgess, Clovis, CA (US)

(73) Assignee: E. & J. Gallo Winery, Modesto, CA (US)

( * ) Notice: Subject to any disclaimer, the term of this patent is extended or adjusted under 35 U.S.C. 154(b) by 349 days.

(21) Appl. No.: 17/154,953

(22) Filed: Jan. 21, 2021

(65) Prior Publication Data

US 2021/0230645 A1    Jul. 29, 2021

Related U.S. Application Data

(60) Provisional application No. 62/965,686, filed on Jan. 24, 2020.

(51) Int. Cl.
| | |
|---|---|
| *C12P 7/22* | (2006.01) |
| *A01H 1/04* | (2006.01) |
| *A01H 5/10* | (2018.01) |
| *A01H 6/28* | (2018.01) |

(52) U.S. Cl.
CPC .................. *C12P 7/22* (2013.01); *A01H 1/04* (2013.01); *A01H 5/10* (2013.01); *A01H 6/28* (2018.05)

(58) Field of Classification Search
None
See application file for complete search history.

(56) References Cited

U.S. PATENT DOCUMENTS

| | | | | |
|---|---|---|---|---|
| 9,718,065 | B1* | 8/2017 | Cilia | B01D 11/0219 |
| 2005/0249837 | A1* | 11/2005 | Massimino | A23K 50/40 |
| | | | | 426/52 |
| 2007/0104842 | A1 | 5/2007 | Margolis et al. | |
| 2013/0122146 | A1* | 5/2013 | Ghaedian | A23L 19/105 |
| | | | | 426/634 |
| 2017/0079933 | A1* | 3/2017 | Whittle | A61K 36/185 |
| 2019/0336521 | A1* | 11/2019 | Kotra | A61K 31/775 |
| 2020/0009109 | A1 | 1/2020 | Macaluso et al. | |

FOREIGN PATENT DOCUMENTS

| | | |
|---|---|---|
| CN | 109996551 A | 7/2019 |
| WO | WO-2018061009 A1 | 4/2018 |
| WO | WO-2019119153 A1 | 6/2019 |
| WO | WO-2019211797 A1 | 11/2019 |

OTHER PUBLICATIONS

International Search Report and Written Opinion for PCT/US2021/014461 dated May 13, 2021 (21 pages).

* cited by examiner

*Primary Examiner* — Christian L Fronda
(74) *Attorney, Agent, or Firm* — Goodwin Procter LLP

(57) ABSTRACT

Systems and methods are described for processing a plant material, such as *Cannabis* and/or hemp. An example method includes: providing a slurry of plant material; providing an inert gas; adding the slurry and the inert gas to a tank; applying heat and pressure to the slurry inside the tank to generate a processed plant material; removing the processed plant material from the tank; and drying the processed plant material in a dryer to produce a dried product comprising cannabidiol (CBD).

17 Claims, 8 Drawing Sheets

| Sample Number | CONTROL | S12 | Difference | % Difference |
|---|---|---|---|---|
| Moisture (wt%) | 8% | 4.06% | | |
| Decarb Temp (°C) | n/a | 119 | | |
| Decarb Time (min.) | n/a | 100 | | |
| CBD (mg/g dry) | 2.6 | 41.0 | 38.4 | 1477% |
| CBDa (mg/g dry) | 37.0 | 0.29 | -36.7 | -99% |
| Total CBD (mg/g dry) | 35.05 | 41.0 | 6.0 | 17% |

FIG. 2

METHODS FOR PROCESSING PLANT MATERIALS AND PRODUCING DRIED PRODUCTS

CROSS-REFERENCE TO RELATED APPLICATIONS

This application claims the benefit of U.S. Provisional Patent Application No. 62/965,686, filed Jan. 24, 2020, the entire contents of which are incorporated by reference herein.

TECHNICAL FIELD

The following disclosure relates to systems and methods for processing hemp, *Cannabis*, or other plant materials for stabilization purposes and, in some examples, to techniques for processing and stabilizing one or more cannabinoids obtained from the plant materials.

BACKGROUND

With the rise in popularity of hemp and related plants, the need for improved techniques for extraction of cannabinoids, including cannabidiol (CBD) and tetrahydrocannabinol (THC), continuously grows.

Current methods for cannabinoid extraction generally involve wet, or at the very least damp, harvesting. This wet harvesting may be followed by a drying procedure in which the still-wet plant, received from the wet harvesting method, may be dried in ovens or hung upside down in direct sunlight. Drying the plant after harvesting can prevent mold or other degradation to the plant material; however, this industry standard technique (e.g., drying followed by CBD extraction) can have a negative effect on the final product. For example, use of high-temperature ovens and/or long-term sunlight for drying harvested plants can reduce cannabinoid content or concentrations in the final product (e.g., at least a 2-15% decrease in cannabinoid output).

SUMMARY

In general, in one aspect, the subject matter of this disclosure relates to a method and a system for processing plant material, as well as compositions and products obtained from the method and system. An example method includes: providing a slurry of plant material; providing an inert gas; adding the slurry and the inert gas to a tank; applying heat and pressure to the slurry inside the tank to generate a processed plant material; removing the processed plant material from the tank; and drying the processed plant material in a dryer to produce a dried product comprising cannabidiol (CBD).

These and other objects, along with advantages and features of embodiments of the present invention herein disclosed, will become more apparent through reference to the following description, the figures, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 2 includes a table comparing an industry-standard control sample to a sample derived using the systems and methods described herein, according to some embodiments.

DETAILED DESCRIPTION

Figure 1:
FIG. 1 is a schematic diagram depicting biosynthetic pathways for various cannabinoids, according to an exemplary embodiment.

It is contemplated that apparatus, systems, methods, and processes of the claimed invention encompass variations and adaptations developed using information from the embodiments described herein. Adaptation and/or modification of the apparatus, systems, methods, and processes described herein may be performed by those of ordinary skill in the relevant art.

It should be understood that the order of steps or order for performing certain actions is immaterial so long as the invention remains operable. Moreover, two or more steps or actions may be conducted simultaneously.

Embodiments of the systems and methods described herein relate to processing plant materials for purposes of extracting, generating, and/or stabilizing one or more plant compounds, including cannabinoids. In some examples, plant materials such as hemp and/or *Cannabis* can be pre-processed to produce a slurry of plant particles and water. The slurry can be added to a tank along with an inert gas (e.g., nitrogen). The slurry can be heated and pressurized in the tank to perform a decarboxylation process, which can generate or modify one or more cannabinoid compounds present in the slurry. For example, the decarboxylation process can convert acid-form cannabinoids (e.g., cannabidiolic acid or CBDA) to corresponding neutral-form cannabinoids (e.g., CBD). Once the decarboxylation process is complete, the processed slurry can be removed from the tank and dried in a dryer. Compared to prior techniques, the system and methods described herein are able to achieve a final product having considerably higher concentrations of CBD and/or other cannabinoids. The final product is stable and can be stored without refrigeration or near room temperature for many days, weeks, or months, prior to further processing. Additionally, in various examples, the systems and methods described herein can provide or achieve: an improved yield of terpenes and cannabinoids from plant materials; an increased capacity at downstream extractors; removal of harvest-related demand peaks (e.g., by stabilizing materials for long-term storage); and/or improved yield during extraction by way of generating CBD/THC flakes.

Disclosed herein are exemplary embodiments of methods and supporting systems that facilitate pre-processing and stabilization of plant biomass for an improved downstream cannabinoid extraction. These systems and methods can avoid drying harvested plants in high-temperature ovens and/or direct sunlight, which can contribute to loss in cannabinoid potency of a plant's biomass. Additionally or alternatively, the systems and methods can avoid undesirable evaporation and/or oxidation (e.g., during decarboxylation), which can result in loss of certain cannabinoids, such as cannabidiolic acid (CBDA). In various examples, "Cannabis" can refer to a genus of plants in the Cannabaceae family, including but not limited to the following species: Cannabis sativa, Cannabis indica, and Cannabis ruderalis. In various examples, "hemp" may be synonymous with "Cannabis" or may refer to varieties of Cannabis that are associated with non-drug use (e.g., non-medicinal use or non-psychoactive use). The Cannabis or hemp plant materials described herein and any products or intermediate materials derived therefrom are preferably compliant with all applicable laws and regulations. It is understood, however, that the applicable laws and regulations can vary among jurisdictions, such that plant materials, products, or materials that may qualify as being compliant in one jurisdiction may not qualify as being compliant in another jurisdiction.

In various examples, to prepare plant material for drying (e.g., in a refractance window dryer), a fresh harvested plant may be pre-processed to ensure that materials handled by the dryer have appropriate characteristics, including moisture content and/or cannabidiol (CBD) content. For example, after harvesting, a plant biomass may be destemmed, chopped, and/or milled into a slurry biomass material. Before drying, the slurry may be processed under heat and pressure in a decarboxylation procedure in which cannabinoids, tinctures, and/or other similar extractable materials may be converted prior to drying. This conversion (e.g., of CBDA to CBD) can prevent deterioration of the cannabinoids and tinctures and, therefore, can improve an overall yield or extraction from the plant material. The drying of the slurry (e.g., in a refractance window dryer) may stabilize the plant biomass and lock in a higher cannabinoid extract or other tincture potency. This stabilization can prevent deterioration of the resulting product, for example, during storage for long-time preparation or for non-peak demand periods. Advantageously, the systems and methods described herein can provide not only a better shelf life through stabilization, but can also eliminate the need for refrigeration. For example, the final, stabilized product produced using the systems and methods can survive at or near room temperature (e.g., from about 15° C. to about 25° C., or about 20° C.) with little or no deterioration in CBD content or other characteristics for several days, weeks, months, or years (e.g., 5 years or more).

By comparison, with prior or existing processes, harvested plants may be subjected to high temperatures (e.g., in a hot oven or combustion) or UV radiation (e.g., in direct sunlight) that can damage a chemical complex of the plant. For example, such prior processes can subject plants to high temperatures under which a spontaneous loss of cannabinoids may occur. For example, phytocannabinoids in dried Cannabis can carry a carboxylic acid moiety that can be lost spontaneously when subjected to high temperature (e.g., resulting from direct sunlight, a hot oven, or similar heat sources).

FIG. 1 illustrates example biosynthetic pathways occurring within Cannabis plants for various cannabinoids, including phytocannabinoids, according to an exemplary embodiment. Cannabigerolic acid (CBGA) 102 generally serves as a key branching point for the biosynthesis of many cannabinoids, such as $\Delta^9$-THC 104, cannabielsoin (CBE) 106, cannabichromene (CBC) 108, and cannabicyclol (CBL) 110 families of phytocannabinoids. Standard biosynthesis procedures provide that CBGA 102 may be synthesized from geraniol and C12-polyketides catalyzed by CBGA synthase in Cannabis. This biosynthetic pathway can include four types of reactions: enzyme catalysis, thermal reaction, oxidation, and irradiation. The conversion of CBGA 102 into $\Delta^9$-Tetrahydrocannabinolic acid ($\Delta^9$-THCA) 112, cannabidiolic acid (CBDA) 114, and cannabichromenic acid (CBCA) 116 is catalyzed by corresponding synthases, as demonstrated in FIG. 1. CBCA 116 and CBC 108 can be further converted to cannabicyclolic acid (CBLA) 118 and CBL 110, respectively, when exposed to photo-irradiation (e.g., UV light). $\Delta^9$-Tetrahydrocannabinol ($\Delta^9$-THC) 104 can be transformed into cannabinol (CBN) 120 through an oxidative aromatization, and CBN 120 can be photochemically rearranged into catechol, cannabinodiol (CBND) 122.

In various examples, an "acid form" of a cannabinoid can refer to an acid moiety of a cannabinoid, such as a carboxylic acid moiety or a cannabinoid having a carboxyl group. Acid-form cannabinoids can include, for example, CBDA, CBCA, CBGA, and THCA.

In various examples, a "neutral form" or "non-acid form" of a cannabinoid can refer to a moiety of a cannabinoid that is not acidic or does not have a carboxyl group. Neutral-form cannabinoids can include, for example, CBD, CBC, CBG (Cannabigerol), and THC. In general, the acid forms of cannabinoids tend to be more volatile or prone to evaporation, compared to the neutral forms of cannabinoids.

In certain examples, the present systems and methods use a pressurized tank to prevent evaporation and/or unwanted oxidation, which can cause loss or deterioration of cannabinoids, such as CBDA. The systems and methods can prevent oxidation by displacing oxygen in the tank with an inert gas, such as nitrogen and/or argon. By pressurizing the tank before heating the plant biomass (e.g., including hemp and/or Cannabis), evaporative loss of cannabinoids including CBDA (e.g., the acid form of CBD) can be avoided, thereby achieving a higher yield of CBD, THC, and/or other desired cannabinoids. The systems and methods can utilize a decarboxylation process that converts the CBDA to CBD and prevents loss of CBDA during the decarboxylation process, so all or nearly all initially available CBDA is converted to CBD. Additionally or alternatively, one or more other acid forms of cannabinoids (e.g., in addition to or instead of CBDA) can be converted during the decarboxylation process, such as the conversion of CBLA to CBL, CBCA to CBC, CBGA to CBG, CBEA (cannabielsolic acid) to CBE, THCA to THC, and the like. In some implementations, the decarboxylation process can convert at least 80%, at least 90%, at least 95%, or at least 99% of CBDA (or other acid forms of cannabinoids) initially present in the plant material to CBD (or other corresponding neutral forms of cannabinoids). In one example, 100% of the initially present CBDA can be converted to CBD during the decarboxylation process. After the conversion from CBDA to CBD is completed (and/or after other acid forms of cannabinoids have been converted to corresponding neutral forms), the biomass can be cooled, depressurized, and dried.

After drying, the resulting CBD/THC flakes can be stable at ambient or room temperatures, thereby facilitating storage, transportation, and/or use of the flakes. The resulting flakes can include stable or neutral forms of any corresponding acid forms of cannabinoids that were present in the original plant material and converted during the decarboxylation process. All such neutral cannabinoids can be available for subsequent extraction. Composition ranges for the cannabinoids in the flakes can be based on the composition of the original plant material. Advantageously, most or all (e.g., greater than 80%, 90%, 95%, or 99%) of the acid-form cannabinoids present in the original plant material can be stabilized by the decarboxylation process described herein and preserved in the resulting flakes (e.g., as corresponding neutral form cannabinoids). By comparison, previous or existing processing methods can lose large amounts (e.g., 50%, 75%, 90%, or more) of the volatile acid cannabinoid content in the plant material (e.g., before these cannabinoids can be converted to stable, neutral forms). This can result in a significant decrease in cannabinoid potency of resulting products.

FIG. 2 includes a table 200 comparing output of an industry-standard control sample ("Control 1") to a sample of a dried sample produced by the systems and methods ("S12") described herein, according to some embodiments. The table 200 lists amounts of moisture, CBD, and CBDA present in the control sample and in the sample product. For example, the table 200 indicates that the control sample had a moisture content of 8%, by weight, and the sample product had a moisture content of about 4%, by weight. More importantly, however, the industry-standard control sample had about 2.6 mg/g (dry basis) of neutral CBD and about 37.0 mg/g (dry basis) of CBDA. By comparison, the sample produced by the systems and methods described herein had about 41.0 mg/g (dry basis) of CBD and about 0.29 mg/g (dry basis) of CBDA. Thus, the sample produced by the systems and methods described herein (S12) represents an increase in CBD yield of about 1477% (e.g., (41.0−2.6)/2.6*100=1477), compared to the industry standard. Additionally, a mass ratio of CBD/CBDA was considerably higher in the sample produced by the systems and methods described herein (e.g., 141 vs. 0.070), indicating that the systems and methods achieve much higher rates of conversion for CBDA to CBD.

Figure 3:
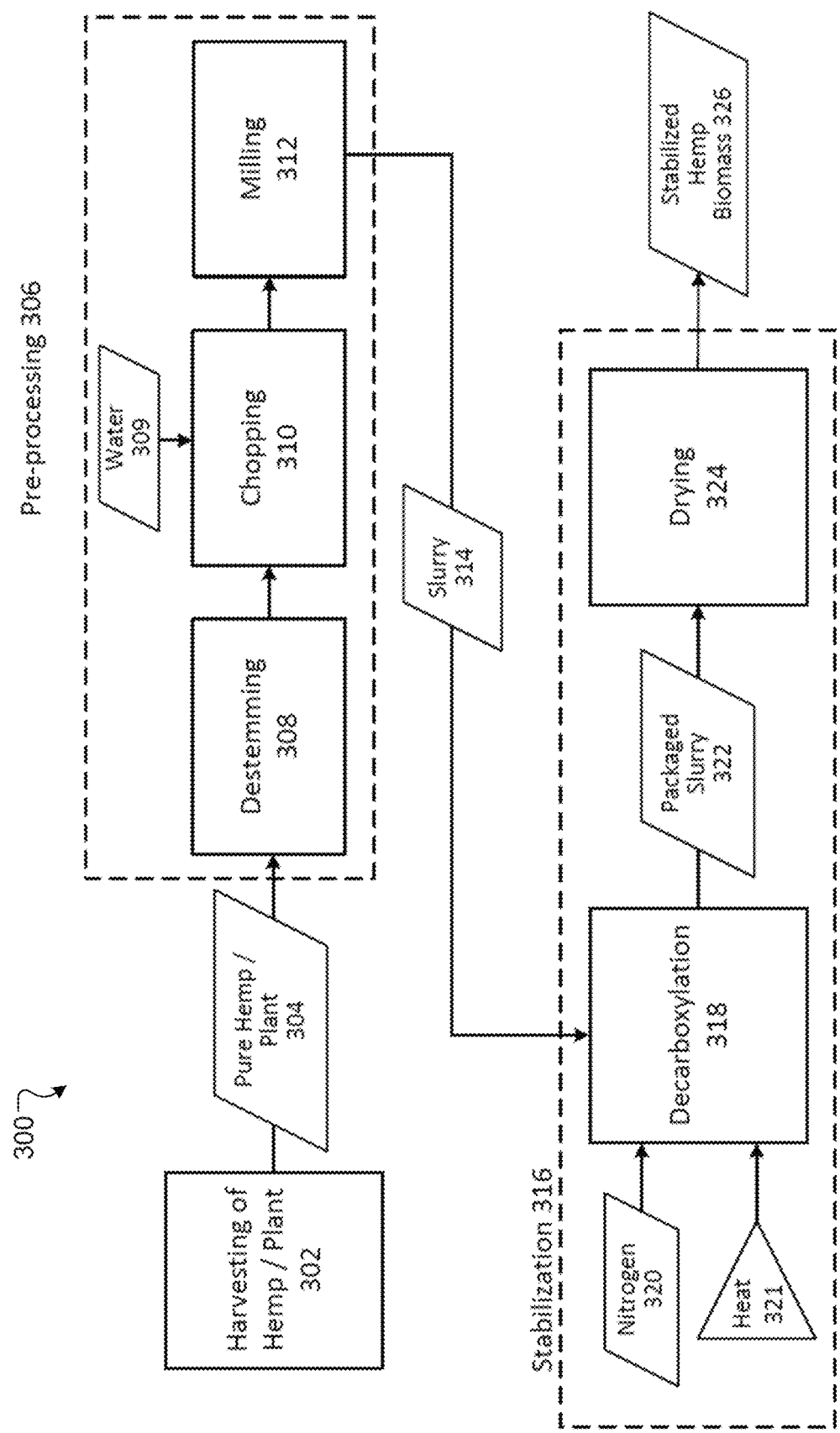
FIG. 3 is a schematic workflow diagram of an exemplary method for pre-processing and stabilizing fresh hemp, according to an exemplary embodiment.

FIG. 3 illustrates a schematic workflow diagram of an exemplary method 300 for pre-processing and stabilizing fresh hemp and/or other plant materials, according to some embodiments. Method 300 includes harvesting (step 302) plants such as, for example, hemp, *Cannabis*, other plants with extractable solutes, or any combinations thereof, according to some embodiments. The method 300 shown in FIG. 3 includes harvesting a pure hemp plant at step 302. The harvested pure hemp 304, which contains CBDA, CBGA, and/or various other cannabinoids or components, may then be subjected to pre-processing (step 306). In some examples, the harvested hemp 304 can be pre-processed while the hemp 304 is still fresh (e.g., within a few hours or days of harvesting) or before the harvested hemp 304 has had a chance to degrade (e.g., through loss of acid-form cannabinoids) or lose moisture (e.g., through evaporation during drying). Alternatively or additionally, the pure hemp 304 can be packaged, cooled, or otherwise preserved in a manner that avoids or minimizes such degradation or evaporation. In various examples, the amounts, distribution, and/or types of cannabinoids (e.g., CBDA, CBGA, etc.) present in the harvested pure hemp 304 and/or in other materials produced using the systems and methods described herein can depend on the types of plant materials (e.g., breeds, varieties, etc.) included in the harvested pure hemp 304.

According to some embodiments, pre-processing (step 306) may include at least one or more of the following procedures: destemming (step 308), chopping (step 310), and milling (step 312). Destemming (step 308) may include an automated destemming process (e.g., using a destemmer machine) in which the stems of each harvested plant can be removed from other portions of the plant, including, for example, any leaves, flowers, or buds. Chopping (step 310) may be accomplished through various mechanisms (e.g., a rough grinder and/or a fine grinder) and may utilize an automated chopping device and/or may involve adding or including water 309 (or other suitable liquids), to facilitate chopping and mixing of plant materials, according to some embodiments. Similarly, milling (step 312) may include an automated milling device (e.g., a BOSTON shear colloidal mill) and may produce a biomass slurry 314 of plant material particles suspended in water. In some examples, plant material particle sizes (e.g., diameters) for the slurry may be from about 150 microns to about 450 microns, on average and/or including minimum and maximum particle sizes. Such particle sizes can enable the slurry to support an increased suspended solids ratio, which can reduce the need for water to be included in the slurry to achieve a proper viscosity. Achieving the proper viscosity with less water can provide for a more efficient pre-processing procedure compared to the current state of the art. Proper viscosity and less water can also facilitate drying of the plant material during subsequent drying processes. For example, a proper viscosity can allow the plant material to flow or be formed into a uniform sheet or layer for drying. In various examples, the slurry 314 can include about 50%, about 75%, about 90%, or more, water or moisture by weight, with the remainder being plant material (e.g., solids). Additionally or alternatively, the plant material present in the slurry 314 can include at least 50%, at least 75%, at least 90%, at least 95%, or 100% of the cannabinoid materials (e.g., by weight) that were present in the harvested pure hemp 304.

According to some embodiments, pre-processing (step 306) may export the biomass slurry 314 to be further stabilized by a stabilization procedure (step 316), which may include a decarboxylation process (step 318). The decarboxylation process (step 318) may receive the slurry 314, an inert gas 320 (e.g., nitrogen and/or argon), and heat energy 321 (e.g., delivered using a heating coil or tube), according to some embodiments. The decarboxylation process (step 318) can generate individual packages or containers (e.g., bottles or 55 gallon drums, preferably coated with a liner of polyethylene or other polymer) of slurry, shown as packaged slurry 322 in FIG. 3. The slurry in the packaged slurry 322 can have physical characteristics that make the slurry ready to be received by a drying process 324, which can include a dryer (e.g., a refractance window dryer). According to some embodiments, these physical characteristics of the slurry may be or include, for example, a particle size ranging from 150 to 450 microns to enable an ideal viscosity for drying. Additionally or alternatively, a moisture content of the slurry in the packaged slurry 322 can be, for example, from about 85% to about 95%, by weight. The drying process (step 324) can be accomplished through various mechanisms and typically involves use of heat and/or dry air to reduce a moisture content of the packaged slurry 322. The drying process (step 324) may be a final step in the stabilization procedure (step 316) and, as such, may produce a stabilized plant biomass, such as a stabilized hemp biomass 326. Once a plant biomass is stabilized, the biomass may no longer be susceptible to mold, biodegrading effects, or potency degradations more generally.

Figure 4:
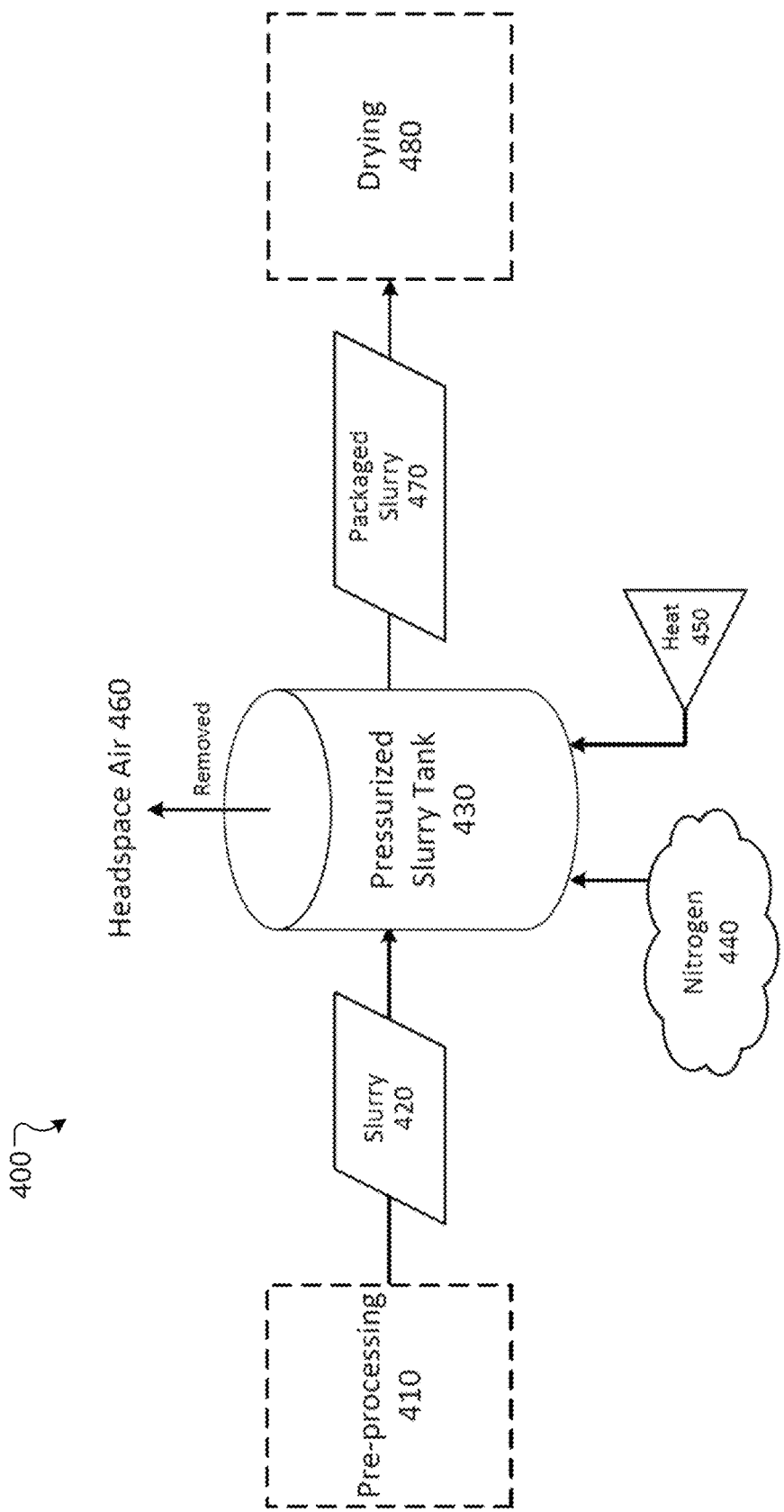
FIG. 4 is a schematic workflow diagram of an exemplary method for performing a decarboxylation procedure, according to an exemplary embodiment.

FIG. 4 illustrates a schematic workflow diagram of an exemplary method 400 for performing a decarboxylation process (e.g., the decarboxylation process 318) according to some embodiments. After pre-processing procedures 410 have completed, as described herein (e.g., for pre-processing 306), slurry 420 can be stored in a pressurized tank, such as a slurry tank 430, according to FIG. 4. Once slurry 420 has been stored in the slurry tank 430, nitrogen 440 (or other inert gas) can be injected into the slurry tank 430 by way of an injection point (e.g., a nozzle). By adding nitrogen 440 to the slurry tank 430, the nitrogen 440 may blanket or surround the slurry 420 inside slurry tank 430, such that any other gases (e.g., air) can be removed from a headspace of the slurry tank 430. The addition of nitrogen 440 may also facilitate pressurization of the slurry tank 430, which can help prevent or avoid evaporation of water or other volatile constituents (e.g., CBDA, CBGA, THCA, and/or other volatile acid cannabinoid forms) within the slurry tank 430. Heat energy 450 may also be provided to the slurry tank 430, for example, using a heating coil or tube heated with steam or electrical energy, according to some embodiments. Headspace air 460 (e.g., above the slurry 420 in the slurry tank 430) may be removed through an extraction point, which can be located at a top portion of the slurry tank 430 and/or can be separate from the injection point where nitrogen 440 is injected. Once nitrogen 440 has been blanketed inside the slurry tank 430 and headspace air 460 has been removed, the slurry tank 430 may be sealed and pressurized with the nitrogen 440. Pressurizing with nitrogen 440 may prevent evaporation and, ultimately, can reduce losses of cannabinoids or other volatile constituents in the slurry 420. After being pressurized and heated, the decarboxylation process (e.g., the decarboxylation process 318) can be performed on the slurry 420 in the slurry tank 430, according to some embodiments. The decarboxylation process can convert one or more acid-form cannabinoids present in the slurry 420 to neutral-form cannabinoids (e.g., convert CBDA to CBD, CBGA to CBG, CBLA to CBL, and/or CBEA to CBE, as described herein). After completing the decarboxylation process, a processed slurry may be removed from the slurry tank 430 and packaged by a packaging device to produce a packaged slurry 470, according to some embodiments. For example, the processed slurry can be pumped out of the slurry tank 430 and packaged in 55 gallon drums or other containers. The packaged slurry 470 may then be ready for a drying procedure (step 480) (e.g., the drying process 324), according to some embodiments.

In some examples, the decarboxylation process can be or include a batch process in which all ingredients (e.g., the slurry 420 and nitrogen 440) are added to the slurry tank 430, the slurry tank 430 is sealed, decarboxylation is achieved through pressure and heat for a predetermined time period, the slurry tank 430 is unsealed, and the processed slurry is removed and packaged. The slurry tank 430 for the batch process can be or include, for example, a pressure reactor, a pressure vessel, a pressure tube, or a sealed tube. Alternatively or additionally, the decarboxylation process can be or include a continuous process in which ingredients (e.g., the slurry 420 and nitrogen 440) are added continuously to the slurry tank 430, decarboxylation is performed in the slurry tank 430 through the application of pressure and heat, and processed slurry is continuously removed from the slurry tank 430 for packaging. The slurry tank 430 for the continuous process can be or include, for example, a continuous stirred tank reactor. A pressure rating for the slurry tank 430 is preferably 50 psig or greater.

Figure 5:
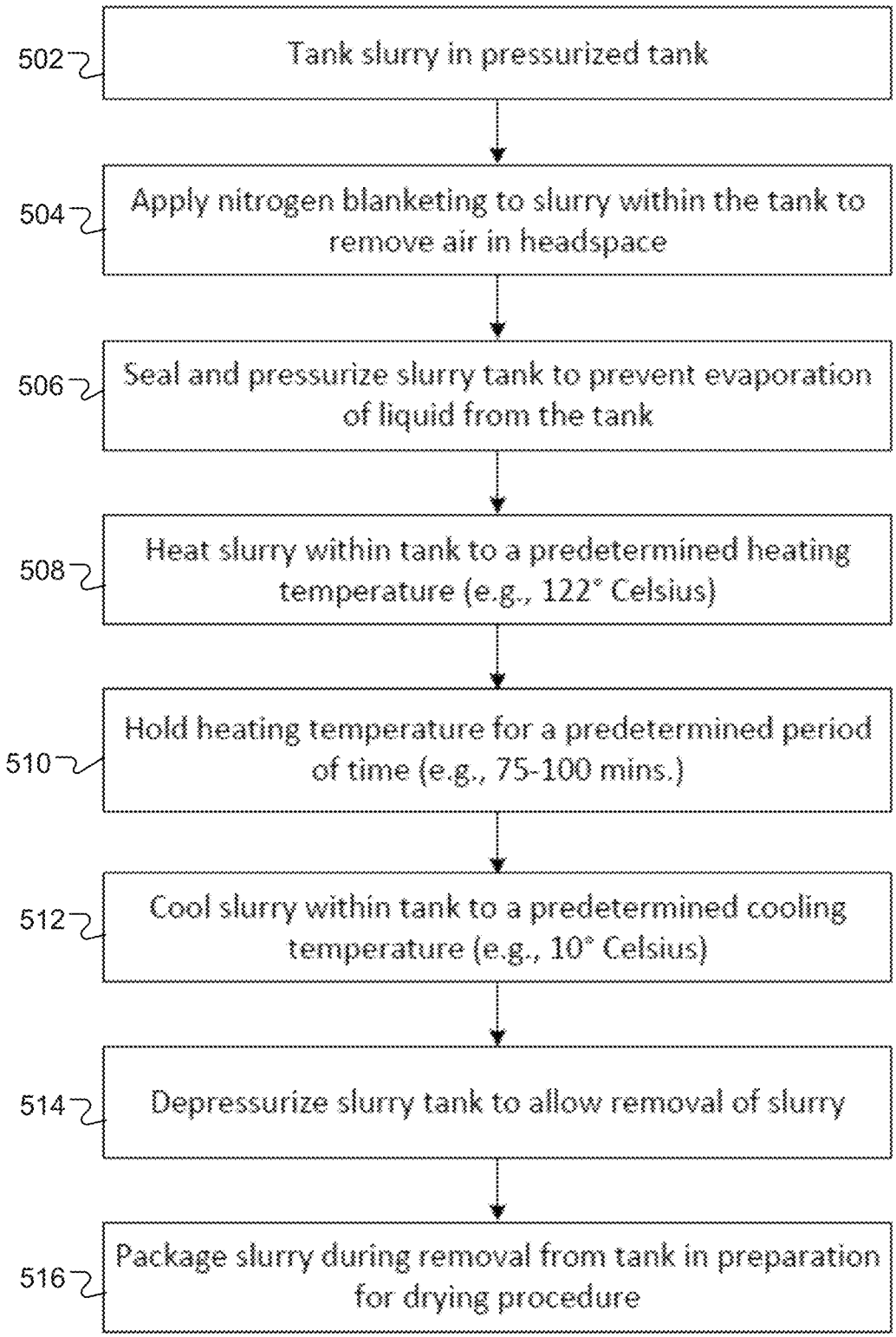
FIG. 5 is a flowchart of an exemplary method for performing a decarboxylation procedure, according to an exemplary embodiment.

FIG. 5 illustrates a flowchart of an exemplary method 500 for performing a decarboxylation process (e.g., the decarboxylation process 318), according to some embodiments. Method 500 includes receiving slurry (e.g., the slurry 420) from a pre-processing device and tanking (step 502) the slurry in a tank (e.g., the slurry tank 430). The tank may hold, for example, about 2,200 gallons, such that if the tank is 80% full the tank may hold about 1,760 gallons of slurry, according to some embodiments. Method 500 includes applying (step 504) nitrogen (e.g., nitrogen 440) to the tanked slurry. According to some embodiments, approximately 60 cubic feet of nitrogen may be enough to displace the air in the tank's headspace, which may occupy about 20% of the tank's volume. This blanketing of nitrogen over the slurry can push air or other gases from the headspace or other regions of the tank. The nitrogen may be applied to the tank by way of an insertion point, as described herein. The headspace air may be removed through a removal point, also described herein. Method 500 further includes sealing (step 506) the slurry tank, according to some embodiments. Once sealed, the slurry tank may then be pressurized to prevent evaporation or sublimation of materials in the tank. For example, at 122° C., the pressurization may increase the pressure inside the tank (e.g., a vapor pressure) by about 5 psi, according to some embodiments. For example, if the pressure inside the tank starts at about 16 psig, the pressurization may bring the internal pressure of the tank up to about 21 psig. In some examples, the pressure in the tank can increase from about 5 psig to about 48 psig as the tank contents are heated (e.g., from about 20° C. to about 120° C., e.g., over a period of about 90 minutes). The higher pressure and temperature can be maintained in the tank for a desired period of time, such as about 70 minutes. The pressure can decrease back to 5 psig when the contents are cooled (e.g., over a period of about 50 minutes), prior to depressurizing.

Once the tank is prepared for temperature changes (e.g., sealed and pressurized), the slurry in the tank may be heated (step 508) to a predetermined heating temperature. For example, the slurry may be heated to a predetermined heating temperature of 122° C., according to some embodiments. This predetermined heating temperature (e.g., 122° C.) may be held (step 510) for a predetermined period of time. For example, the slurry may be held at a constant predetermined heating temperature (and pressure) for a predetermined period of time from about 25 minutes to about 105 minutes, or for about 70 minutes, according to some embodiments.

After maintaining a desired slurry temperature and pressure in the tank for a desired period of time, a cooling procedure can be used to cool (step 512) the slurry to a predetermined cooling temperature. For example, the slurry may be cooled to a predetermined cooling temperature of about 20° C., or from about 10° C. to about 30° C., according to some embodiments. This predetermined cooling temperature (e.g., 20° C.) may be held for a predetermined period of time. For example, the slurry may be held at a constant predetermined cooling temperature for a predetermined period of time (e.g., about 5 minutes, 15 minutes, or 30 minutes, more or less), according to some embodiments.

After cooling (step 512), the slurry tank may be depressurized (step 514), according to some embodiments. The slurry may then be removed from the tank and properly packaged (step 516) in preparation for an upcoming drying procedure, as described herein, which can be performed in a refractance window dryer or other type of dryer.

Figure 6:
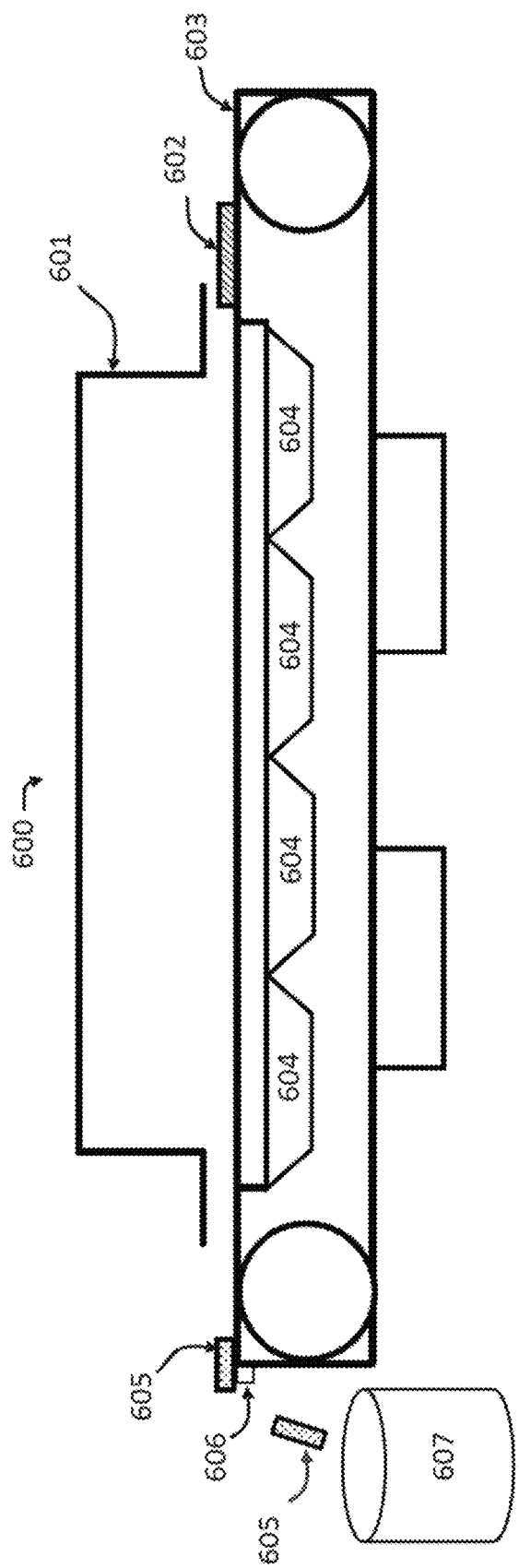
FIG. 6 is a schematic side view of a refractance window dryer, according to an exemplary embodiment.

FIG. 6 illustrates a schematic side view of a refractance window dryer 600, according to some embodiments. The dryer 600 may have a long tunnel 601, typically formed from stainless steel and suitable for rapid water evaporation. Pre-processed plant biomass (e.g., packaged slurry 322 or packaged slurry 470) may pass through tunnel 601 as a slurry 602 at a particular speed on a top surface of a belt 603, which can be made of mylar or other suitable materials. Hot water circulates through shallow heating trays 604 underneath the belt 603 and heats the slurry 602, according to one embodiment. The pre-processed biomass or slurry 602 may have a beginning moisture level from about 65% to about 95%, by weight, or from about 85% to about 95%, by weight, according to some embodiments. Additionally or alternatively, the pre-processed biomass or slurry 602 may have a beginning solids content (e.g., including decarboxylated plant material) from about 5% to about 35%, by weight, or from about 5% to about 15%, by weight.

A dried product can exit the tunnel 601 as a stabilized biomass 605, which may be removed from the mylar belt 603 by a removal blade or edge 606 placed in contact with the mylar belt 603 at a bullnose end of the dryer. According to some embodiments, the stabilized biomass 605 may have a final moisture level from about 2.5% to about 8%, by weight. Additionally or alternatively, the stabilized biomass 605 may have a solids content from about 92% to about 97.5%, by weight. The stabilized biomass 605 can be or include, for example, CBD and/or THC flakes. Contact with removal edge 606 may cause biomass 605 to reliably lift from the belt 603 and drop into a collection container 607. According to some embodiments, biomass 605 may be maintained at an ambient holding temperature within the collection container 607, eliminating the need for maintaining a particular preservation temperature. Plastic bags or final packaging may be placed inside collection containers for final preparation of the biomass 605 for inventory storage or shipping for extraction.

In some examples, a level of homogenization can be important to achieve proper drying of the slurry 602. For example, particles in the slurry 602 should be small enough to stay in solution and/or suspension for drying; otherwise, the slurry structure may deteriorate or fall apart during the drying process. If homogenization is not done properly, for example, the slurry 602 can be applied unevenly and/or form thick and thin spots on the belt. This can require a reduction in belt speed to achieve adequate drying, which can decrease yield. Additionally or alternatively, if the stabilized biomass 605 is not dry enough, the stabilized biomass 605 can stick to the belt 603 and/or may not be sufficiently stable at room temperature (e.g., due to mold or mildew).

In various implementations, the stabilized biomass 605 can be used directly as a consumable product ingredient (e.g., in food, animal feed, smokable products, etc.). Alternatively or additionally, the stabilized biomass 605 can be used in extraction processes for cannabinoid production and related products. The extraction processes can utilize or include, for example, extraction using $CO_2$ (e.g., supercritical $CO_2$ extraction) or one or more solvents, such as water, ethanol, propane, butane, heptane, pentane, or any combination thereof. Such solvents can extract and/or dissolve one or more cannabinoids that are present in the stabilized biomass 605, and the extracted or dissolved cannabinoids can be subsequently removed from solution (e.g., by evaporating the solvent).

In some instances, for example, the stabilized biomass 605 or portions thereof can be used to produce a nutraceutical product, a pharmaceutical product, a therapeutic product, a healthcare product, or other consumer product. For example, the stabilized biomass 605 or portions thereof can be combined in an extractor unit with one or more solvents (e.g., water, an alcohol, an alkane, and/or an oil) to extract cannabinoids or other materials from the stabilized biomass 605. The extracted materials can be combined with one or more other ingredients (e.g., in a mixer) to form a consumer product that includes one or more cannabinoids, such as CBD. The consumer product can be or include, for example, an edible product (e.g., a pill, tablet, or food product) or a topical product, such as a lotion, a cream, a salve, or an ointment.

Figure 7:
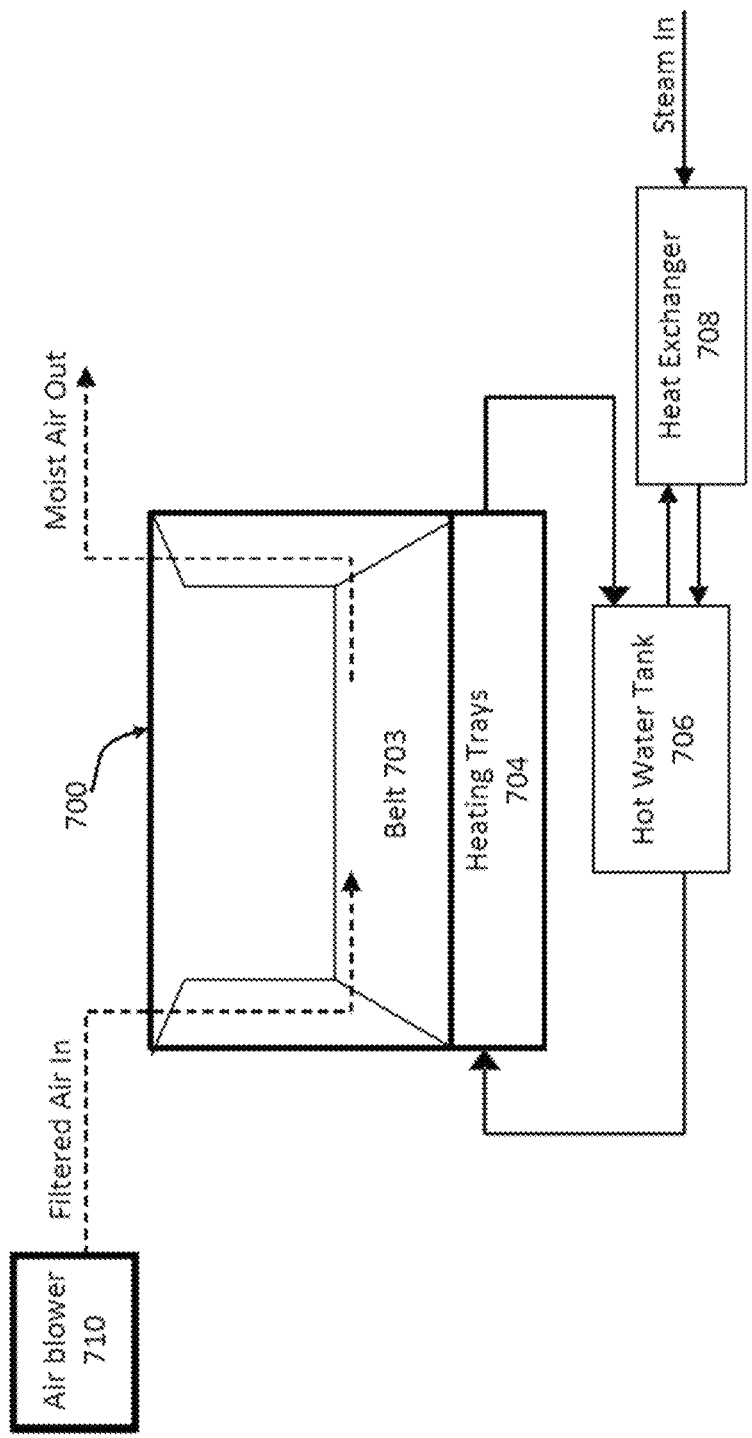
FIG. 7 is a schematic cross-sectional end view of a refractance window dryer, according to an exemplary embodiment.

FIG. 7 illustrates a cross-sectional view of air and water circulation components for a refractance window dryer 700, which can be the same as dryer 600 or include some or all elements of dryer 600. Hot water circulates through shallow heating trays 704 underneath a conveyor belt 703 (e.g., belt 603) and heats the packaged slurry (e.g., the slurry 602), according to one embodiment. Thermal energy from the hot water can be transmitted through the conveyor belt 703 to the slurry (e.g., via conduction, convection, and/or radiation). The hot water can have a temperature of up to about 210° F. (about 99° C.) or any temperature suitable to dry the slurry to a desired moisture content. In some instances, soft water can be used for the water in the heating trays 704 under belt 703, to avoid staining and/or deposits on the stainless steel or other system components, which can reduce drying efficiency. The water is typically held in one or more tanks underneath the belt 703, such as a hot water tank 706. The hot water tank 706 can be connected to a heat exchanger 708 that can use steam to reach and maintain an adjustable set point temperature. Other heat sources, such as electrical heating elements, can be used to achieve a desired temperature for the hot water.

According to some embodiments, at least one air blower 710 can be used to provide fresh air (e.g., filtered or low humidity air) above the belt 703 and/or to continuously sweep water vapor away from the belt 703 or dryer 700, to achieve a suitable or maximum rate of water evaporation. The combination of evaporative cooling and limited heat conductivity of the belt 703 can keep the packaged slurry from reaching the temperatures of the hot water in the heating trays 704, which could negatively impact product quality. In general, it is desirable to maintain the temperature of the slurry below about 175° F. (79° C.) during the drying process. Air temperatures within the dryer can range from about 70° F. (21° C.) to about 212° F. (66° C.).

Figure 8:
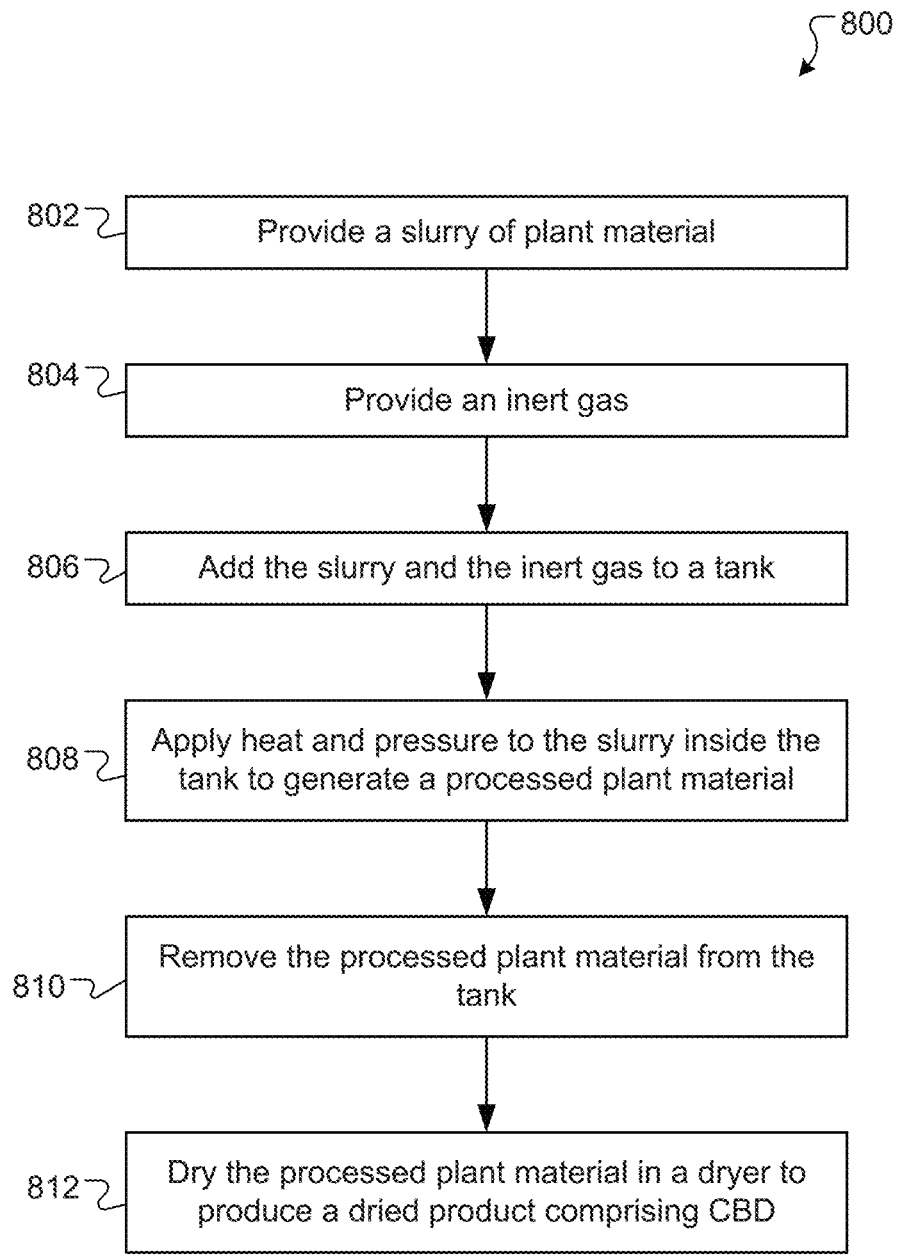
FIG. 8 is a flowchart of an exemplary method of processing plant material, according to an exemplary embodiment.

FIG. 8 is a flowchart of an example method 800 of processing plant material. A slurry of plant material (e.g., including particles of hemp and/or *Cannabis*) is provided (step 802). An inert gas (e.g., nitrogen or argon) is provided (step 804) from a gas source (e.g., a gas tank or line). The slurry and the inert gas are added (step 806) to a tank, which can be, for example, a pressure vessel for performing a decarboxylation process. Heat and pressure are applied (step 808) to the slurry inside the tank to generate a processed plant material. The processed plant material is removed (step 810) from the tank and dried (step 812) in a dryer to produce a dried product comprising CBD and/or one or more other cannabinoids.

Example low, high, and typical range values for various material and process parameters are provided in Table 1. Various embodiments include any parameter value (e.g., integer or decimal value) within the cited ranges. Express support and written description of these parameter values for each parameter are hereby represented.

TABLE 1

Exemplary material and processing parameters.

| Parameter | Low | Typical | High |
|---|---|---|---|
| Plant particle size in slurry before decarboxylation (microns) | 150 | 300 | 450 |
| Plant particle size in slurry after decarboxylation (microns) | 150 | 300 | 450 |
| Viscosity of slurry at 20° C. before decarboxylation (Pa-s) | 100 | 110 | 120 |
| Viscosity of slurry at 20 ° C. after decarboxylation (Pa-s) | 100 | 110 | 120 |
| Decarboxylation slurry temperature (° C.) | 110 | 120 | 130 |
| Decarboxylation slurry pressure (psig) | 45 | 50 | 100 |
| Decarboxylation time (minutes) | 25 | 70 | 105 |
| Drying slurry temperature (° C.) | 60 | 71 | 82 |
| Drying air temperature (° C.) | 38 | 52 | 66 |

Table 2 illustrates example compositions for a slurry of plant material produced using the pre-processing techniques described herein (e.g., the slurry 314 produced by pre-processing 306). Various embodiments include any parameter value (e.g., integer or decimal value) within the cited ranges. For example, the CBD weight percentages can be 0.2, 0.3, 0.4, . . . , 2.9, 3.0. Express support and written description of these parameter values for each parameter are hereby represented. The compositions can include other materials that are not listed in Table 2, such as cellulose or other plant materials.

The weight percentages of cannabinoids listed in Table 2 (and in Tables 3 and 4, below) are on a dry weight basis. These dry basis weight percentages can be converted to wet basis weight percentages using techniques known to those having ordinary skill in the art. In some instances, for example, dry basis weight percentages can be converted to wet basis weight percentages using the following equation: Wet Basis Weight Percentage=Dry Basis Weight Percentage×(100−Moisture Weight Percentage)/100. For example, if the dry basis weight percentage is 1% and the moisture weight percentage is 90%, then the wet basis weight percentage can be: (1)×(100−90)/100=0.1%.

While Table 2 lists only one specific type of acid-form cannabinoid (i.e., CBDA) and one specific type of corresponding neutral-form cannabinoid (i.e., CBD), it is understood that other types of acid-form and neutral-form cannabinoids (e.g., CBGA, CBG, CBCA, CBC, etc.) can be present in the slurry. For example, the weight percentages for any other acid-form cannabinoid can be the same as the weight percentages listed in Table 2 for CBDA. Likewise, the weight percentages for any other neutral-form cannabinoid can be the same as the weight percentages listed in Table 2 for CBD. As described herein, the amounts, distribution, and/or types of cannabinoids present in the slurry can depend on the plant materials used as inputs to the pre-processing step 306 (e.g., hemp plant 304).

TABLE 2

Exemplary composition of slurry produced by pre-processing plant material.

| Ingredient | Low | Typical | High |
|---|---|---|---|
| CBD (wt %, dry basis) | 1 | 1.5 | 5 |
| CBDA (wt %, dry basis) | 5 | 10 | 25 |
| Total neutral form cannabinoids (wt %, dry basis) | 1.5 | 3 | 7.5 |
| Total acid form cannabinoids (wt %, dry basis) | 5.5 | 11.5 | 27.5 |
| Moisture (wt %) | 85 | 92 | 95 |

Table 3 illustrates example compositions for a packaged slurry produced using the decarboxylation techniques described herein (e.g., the packaged slurry 322 produced by decarboxylation 318). Various embodiments include any parameter value (e.g., integer or decimal value) within the cited ranges. Express support and written description of these parameter values for each parameter are hereby represented. Further, Table 3 indicates that certain cannabinoid concentrations can be less than a limit of quantification or "<LOQ." Such <LOQ concentrations may be too small to be measured and/or equivalent to 0%, in some examples. The compositions can include other materials that are not listed in Table 3, such as cellulose or other plant materials.

While Table 3 lists only one specific type of acid-form cannabinoid (i.e., CBDA) and one specific type of corresponding neutral-form cannabinoid (i.e., CBD), it is understood that other types of acid-form and neutral-form cannabinoids (e.g., CBGA, CBG, CBCA, CBC, etc.) can be present in the packaged slurry. For example, the weight percentages for any other acid-form cannabinoid can be the same as the weight percentages listed in Table 3 for CBDA. Likewise, the weight percentages for any other neutral-form cannabinoid can be the same as the weight percentages listed in Table 3 for CBD. As described herein, the amounts, distribution, and/or types of cannabinoids present in the packaged slurry can depend on the plant materials used as inputs to the pre-processing step 306 (e.g., hemp plant 304).

TABLE 3

Exemplary composition of packaged slurry produced by a decarboxylation method.

| Ingredient | Low | Typical | High |
|---|---|---|---|
| CBD (wt %, dry basis) | 5 | 10 | 25 |
| CBDA (wt %, dry basis) | <LOQ | <LOQ | 1 |
| Total neutral form cannabinoids (wt %, dry basis) | 5.5 | 11.5 | 27.5 |
| Total acid form cannabinoids (wt %, dry basis) | <LOQ | <LOQ | 1.5 |
| Moisture (wt %) | 85 | 92 | 95 |

Table 4 illustrates example compositions for a stabilized product produced using the systems and methods described herein (e.g., the stabilized biomass 605). Various embodiments include any parameter value (e.g., integer or decimal value) within the cited ranges. Express support and written description of these parameter values for each parameter are hereby represented. Further, Table 4 indicates that certain cannabinoid concentrations can be less than a limit of quantification or "<LOQ." Such <LOQ concentrations may be too small to be measured and/or equivalent to 0%, in some examples. The compositions can include other materials that are not listed in Table 4, such as cellulose or other plant materials.

While Table 4 lists only one specific type of acid-form cannabinoid (i.e., CBDA) and one specific type of corresponding neutral-form cannabinoid (i.e., CBD), it is understood that other types of acid-form and neutral-form cannabinoids (e.g., CBGA, CBG, CBCA, CBC, etc.) can be present in the stabilized product. For example, the weight percentages for any other acid-form cannabinoid can be the same as the weight percentages listed in Table 4 for CBDA. Likewise, the weight percentages for any other neutral-form cannabinoid can be the same as the weight percentages listed in Table 4 for CBD. As described herein, the amounts, distribution, and/or types of cannabinoids present in the stabilized product can depend on the plant materials used as inputs to the pre-processing step 306 (e.g., hemp plant 304).

TABLE 4

Exemplary composition of a stabilized product.

| Ingredient | Low | Typical | High |
| --- | --- | --- | --- |
| CBD (wt %, dry basis) | 5 | 10 | 25 |
| CBDA (wt %, dry basis) | <LOQ | <LOQ | 1 |
| Total neutral form cannabinoids (wt %, dry basis) | 5.5 | 11.5 | 27.5 |
| Total acid form cannabinoids (wt %, dry basis) | <LOQ | <LOQ | 1.5 |
| Moisture (wt %) | 2.5 | 5 | 8 |

Terminology

The phraseology and terminology used herein is for the purpose of description and should not be regarded as limiting.

The term "approximately", the phrase "approximately equal to", and other similar phrases (e.g., "about"), as used in the specification and the claims (e.g., "X has a value of approximately Y" or "X is approximately equal to Y"), should be understood to mean that one value (X) is within a predetermined range of another value (Y). The predetermined range may be plus or minus 20%, 10%, 5%, 3%, 1%, 0.1%, or less than 0.1%, unless otherwise indicated.

The indefinite articles "a" and "an," as used in the specification and in the claims, unless clearly indicated to the contrary, should be understood to mean "at least one." The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of" "only one of" or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The use of "including," "comprising," "having," "containing," "involving," and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Each numerical value presented herein, for example, in a table, a chart, or a graph, is contemplated to represent a minimum value or a maximum value in a range for a corresponding parameter. Accordingly, when added to the claims, the numerical value provides express support for claiming the range, which may lie above or below the numerical value, in accordance with the teachings herein. Absent inclusion in the claims, each numerical value presented herein is not to be considered limiting in any regard.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The features and functions of the various embodiments may be arranged in various combinations and permutations, and all are considered to be within the scope of the disclosed invention. Accordingly, the described embodiments are to be considered in all respects as only illustrative and not restrictive. Furthermore, the configurations, materials, and dimensions described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A method of processing plant material, the method comprising:
   providing a slurry of plant material, wherein the slurry comprises plant particle sizes from about 150 microns to about 450 microns;
   providing an inert gas;
   adding the slurry and the inert gas to a tank;
   applying heat and pressure to the slurry inside the tank to generate a processed plant material;
   removing the processed plant material from the tank; and
   drying the processed plant material in a dryer to produce a dried product comprising cannabidiol (CBD).

2. The method of claim 1, wherein the plant material comprises at least one of hemp, *Cannabis*, or a combination thereof.

3. The method of claim 1, wherein the inert gas comprises nitrogen.

4. The method of claim 1, wherein applying heat and pressure comprises performing a decarboxylation process on the plant material.

5. The method of claim 1, wherein applying heat and pressure comprises maintaining a process temperature and a process pressure inside the tank for a process time period, wherein the process temperature is from about 110° C. to about 130° C., and wherein the process pressure is from about 45 psig to about 100 psig.

6. The method of claim 5, wherein the process time period is from about 25 minutes to about 105 minutes.

7. The method of claim 1, wherein the dried product comprises a final moisture content from about 2.5% to about 8%, by weight.

8. The method of claim 1, wherein the dried product comprises the CBD in an amount of at least about 5%, by weight, on a dry basis.

9. The method of claim 1, wherein the dried product comprises neutral form cannabinoids in an amount from about 5% to about 28%, by weight, on a dry basis.

10. The method of claim 1, wherein the dryer comprises a refractance window dryer.

11. The method of claim 1, further comprising:
    pre-processing the plant material by performing at least one of destemming, chopping, or milling; and
    adding water to the pre-processed plant material to generate the slurry.

12. The method of claim 1, further comprising extracting a cannabinoid from the dried product.

13. The method of claim 12, wherein extracting the cannabinoid comprises dissolving the cannabinoid in a solvent.

14. The method of claim 1, further comprising incorporating the dried product or a cannabinoid extracted from the dried product into a consumer product comprising at least one of an edible product, a topical product, a nutraceutical product, or a pharmaceutical product.

15. The method of claim 1, wherein the plant material is fresh plant material.

16. The method of claim 1, wherein the slurry has a viscosity at 20° C. from about 100 Pa-s to about 120 Pa-s.

17. The method of claim 1, wherein the dried product comprises cellulose.

* * * * *